United States Patent [19]

Hinz et al.

[11] 4,274,991
[45] Jun. 23, 1981

[54] ALKYL SULPHONIC ACID PHENYL ESTERS SUBSTITUTED BY CARBOXYLIC ACID ESTERS

[75] Inventors: Jürgen Hinz, Krefeld; Karola Brudermanns, Leverkusen, both of Fed. Rep. of Germany

[73] Assignee: Bayer Aktiengesellschaft, Leverkusen, Fed. Rep. of Germany

[21] Appl. No.: 727,644

[22] Filed: Sep. 29, 1976

[30] Foreign Application Priority Data

Oct. 4, 1975 [DE] Fed. Rep. of Germany ....... 2544552

[51] Int. Cl.³ .................... C08K 5/36; C07C 143/68
[52] U.S. Cl. .................... 260/30.8 R; 260/456 P; 260/761
[58] Field of Search ............ 260/456 P, 726, 30.8 R, 260/761

[56] References Cited

U.S. PATENT DOCUMENTS

| 2,610,164 | 9/1952 | Gluesenkamp et al. | 260/456 P |
| 2,610,165 | 9/1952 | Gluesenkamp et al. | 260/456 P |
| 2,689,862 | 9/1954 | Knowles | 260/456 P |

OTHER PUBLICATIONS

Kirk–Othmer, Encyclopedia of Chemical Technology, vol. 15, pp. 737–740 and 754, (1968).

*Primary Examiner*—Nicky Chan
*Attorney, Agent, or Firm*—Connolly and Hutz

[57] ABSTRACT

Alkyl sulphonic acid phenyl esters which are substituted by carboxylic acid esters can be obtained by reacting sulphochlorinated paraffins with hydroxy benzoic acid esters. Said compounds can be used as plasticizers for polymers.

6 Claims, No Drawings

ALKYL SULPHONIC ACID PHENYL ESTERS SUBSTITUTED BY CARBOXYLIC ACID ESTERS

The esters of certain inorganic and organic acids, for example, phosphoric acid, phthalic acid, adipic acid and alkyl sulphonic acid phenyl esters have long been used as plasticisers for PVC and other polymers. Of these esters, alkyl sulphonic acid phenyl esters are characterised inter alia by their favourable gelability, their high resistance to hydrolysis, their low water absorption and their physiological compatibility. Unfortunately, their volatility, their resistance to migration and their resistance to extraction are only average so far as their use as plasticisers is concerned.

The mechanical properties of, for example, plasticised PVC change in the event of prolonged storage either as a result of evaporation or as a result of migration of the plasticiser from the polymer. Accordingly, there is a need to find plasticisers which have a volatility as low as possible and a resistance to migration which is as high as possible.

The so-called polymeric plasticisers, for example polyester plasticisers, gave some excellent results in this respect.

One disadvantage of polymeric plasticisers in relation to monomeric products is their high viscosity which is unfavourable for processing and incorporation into the polymer. Their gelability is also poorer than that of monomeric products.

It has now been found that, by reacting sulphochlorides of the paraffins or paraffin mixtures preferably with chain lengths of from 10 to 18 carbon atoms with hydroxy benzoic acid esters containing 1 to 12 carbon atoms in the ester group, it is possible to obtain alkyl sulphonic acid esters with excellent plasticiser qualities which combine the advantageous properties of monomeric plasticisers, such as good gelability (crit. dissolution temperature), excellent solvent and bitumen resistance, with those of the polymeric plasticisers, such as low volatility, low viscosity and high resistance to migration.

Accordingly, the present invention provides alkyl sulphonic acid esters corresponding to the general formula (I)

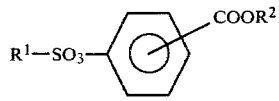

in which
R¹ represents a straight chain or branched chain paraffin radical with 10 to 18 carbon atoms, and
R² represents a straight chain or branched chain alkyl group with 1 to 12 carbon atoms.

The present invention also provides a process for the production of alkyl sulphonic acid phenyl esters corresponding to formula I above by sulphochlorinating paraffin or paraffin mixtures with 10 to 18 carbon atoms by known methods and reacting the resulting alkyl sulphonic acid chlorides with hydroxy benzoic acid esters containing straight-chain or branched chain alkyl groups with 1 to 12 carbon atoms.

The invention also relates to the use of the alkyl sulphonic acid phenyl esters corresponding to formula I above as plasticisers in polymers.

In the formula I which defines the compounds according to the invention, the carboxylic acid ester group is in the two-position and preferably in the three-position or four-position to the sulphonic acid ester group.

Suitable straight chain and/or branched chain paraffins with a chain length of 10 to 18 carbon atoms are, particularly n-paraffins such as decane, undecane, tridecane, tetradecane, pentadecane, hexadecane, heptadecane and octadecane, which boil at temperatures in the range from approximately 170° C. to 320° C. It is preferred to use paraffins with 10 to 13 carbon atoms or 14 to 18 carbon atoms and with boiling ranges of 173° to 234° C. or 252° to 317° C. Mixtures of the above-mentioned paraffins may of course also be used. It is also possible to use mixtures of paraffins obtained by means of molecular sieves or by extraction with urea from petroleum fractions, also hydrogenated kogasin fractions from Fischer-Tropsch's synthesis with a boiling range of 180° C. to 300° C.

Suitable esterification components are hydroxy benzoic acid esters derived from salicylic acid, preferably from 3- or from 4-hydroxy benzoic acid, of which the carboxylic acid ester group contains straight-chain or branched alkyl groups with 1 to 12 carbon atoms and preferably with 2 to 8 carbon atoms. The following are mentioned as examples of alkyl groups: methyl, ethyl, n- and i-propyl, n- and i-butyl, octyl and dodecyl.

The alkyl sulphonic acid esters according to the invention are produced by reacting alkyl sulphochlorides with hydroxy benzoic acid esters. The alkyl sulphochlorides are obtained by sulphochlorinating, the paraffins at a temperature of from 20° C. to 70° C., preferably at a temperature of from 30° C. to 50° C. in the presence of short-wave or visible light. Sulphochlorination is carried out by introducing sulphur dioxide and chlorine into the paraffins. The necessary reaction time for the sulphochlorination reaction is governed by the required degree of sulphochlorination which should amount to between 15 and 80% and preferably to between 25 and 50%. The reaction product obtained by the sulphochlorination reaction, consisting of a mixture of alkyl sulphochloride and unreacted paraffin, is esterified with the hydroxy benzoic acid ester in known manner in the presence of aqueous alkali liquor or gaseous ammonia, from 0.8 to 2 moles and preferably from 0.9 to 1.3 moles of hydroxy benzoic acid ester being used per mole of alkyl sulphochloride.

The reaction has ceased when no more hydrolysable chlorine can be detected. The product of esterification is worked up by washing with water and a dilute alkali liquor, followed by distillation with steam in vacuo. The unreacted paraffin distils off, whilst the sulphonic acid ester of formula I is obtained as the distillation residue, being bleached by treatment with 1 to 5% and preferably with 1.4 to 3% of fuller's earth at a temperature of from 60° to 120° C. and preferably at a temperature of from 80° to 100° C.

The alkyl sulphonic acid phenyl esters of formula I may be used as plasticisers for polymers, for example PVC and for the corresponding copolymers with vinyl esters, such as vinyl acetate, olefins, such as ethylene and propylene, or α,β-unsaturated monocarboxylic and dicarboxylic acid esters, such as acrylates and methacrylates, and natural and/or synthetic rubbers. Depending upon the type of polymer in question, the alkyl sulphonic acid phenyl esters of formula I may be added in a quantity of from 1 to 70 parts and preferably in a quantity of from 10 to 50 parts per 100 parts of polymer. They are incorporated into the polymer by means of the usual mixing machines, such as mixing rolls, kneaders, internal mixers, either on the dry blend principle or in paste form. The incorporation and processing temperatures and times are governed by the particular method adopted. For example, the temperature may be in the range from 20° to 200° C.

The invention is illustrated by the following Examples:

final temperature of 190° C. 370 g of ester (I) were left as distillation residue, being bleached at 80° C. with 7 g of Tonsil. The yield of ester amounted to 365 g.

In Tables 1 and 1a below, the properties of the ester of Example 1 are compared with those of the alkyl sulphonic acid phenyl ester (monomeric plasticiser) and with those of an adipic acid polyester (polymeric plasticiser Ultramoll I (Trade Mark), a product of Bayer AG).

TABLE 1

| Property | Unit | Test method | Alkyl sulphonic acid ester of 4-hydroxy benzoic acid i-octyl ester | Alkyl sulphonic acid phenyl ester | Adipic acid polyester |
|---|---|---|---|---|---|
| Density at 20° C. | g/cm³ | DIN 51757 | 1.028 | 1.042 | 1.08–1.09 |
| Flash point | °C. | DIN 53584 | +272 | +228 | approx. +300 |
| Cold setting point | °C. | DIN 51583 | −40 | −36 | +3 |
| Volatility at 90° C. | | Brabender | | | |
| 0–72 h | % | | −0.2 | −1.8 | −1.0 |
| 48–72 h | % | | ±0 | −0.2 | ±0 |
| Viscosity | mPa.s | DIN 53015 | 425 | 105 | 2000–3000 |
| Crit. dissolution temperature | °C. | Thinius | +143 | +113 | +151 |
| Mechanical properties of PVC-plasticiser mixtures with stabilisers | | | | | |
| Composition: 62.2% PVC, 33.5% plasticiser, 1.4% Ba-Ca-laurate (Irgastab BC 12), 2.9% epoxidised soya bean oil (Estabex 2307) | | | | | |
| Tensile strength | MPa | DIN 53455 | 21.2 | 20.4 | 20.5 |
| elongation at break | kp/cm² | DIN 53455 | 358 | 309 | 336 |
| Cold fracture temperature | °C. | DIN 53372 | −24 | −17 | −15 |
| Volatility, 72h at 90° C. | | Brabender | −0.2 | −1.1 | −0.4 |
| Shore hardness | A/D | DIN 53505 | 85/32 | 80/27 | 85/34 |

TABLE 1a

Plasticiser migration in rigid PVC and polystyrene films (PS) in accordance with DIN 53405

| | Plasticiser migration in % by weight after 1 day | | | | Plasticiser migration in % by weight after 9 days | | | |
|---|---|---|---|---|---|---|---|---|
| | Plasticiser absorbing film against | | Plasticiser-releasing film | | Plasticiser absorbing film against | | Plasticiser-releasing film | |
| | PVC | PS | PVC | PS | PVC | PS | PVC | PS |
| Alkyl sulphonic acid ester of 4-hydroxy benzoic acid i-octyl ester | +0.1 | ±0 | −0.1 | −0.1 | +0.3 | +0.1 | −0.6 | −0.3 |
| Alkyl sulphonic acid phenyl ester | +1.7 | +1.3 | −1.8 | −1.3 | +5.0 | +4.6 | −5.1 | −4.7 |
| Adipic acid polyester | +0.2 | ±0 | −0.3 | −0.1 | +0.8 | ±0 | −1.0 | −0.1 |

EXAMPLE 1

800 g of an n-paraffin mixture with a chain length of from 10 to 18 carbon atoms were reacted at 30° C. with 18 l/h of sulphur dioxide and 16 l/h of chlorine in the presence of light from a 200 watt tungsten filament lamp until a sulphochlorination product containing 4% of hydrolysable chlorine had been formed.

885 g of this sulphochlorination product were mixed with 300 g of 4-hydroxy benzoic acid-i-octyl ester followed by esterification while stirring over a period of about 2 hours at 25° to 30° C. by the dropwise addition of 240 g of 20% sodium hydroxide. The reaction had ceased when no more hydrolysable chlorine could be detected. The reaction mixture was then washed twice with 400 g of 2% sodium hydroxide solution and then once again with 200 g of water at a temperature of from 60° to 70° C. 945 g of crude ester, a mixture of the ester of formula I and paraffin which did not react during sulphochlorination, were separated off and dried with 10 g of Tonsil. The paraffin was then distilled off with steam under a vacuum of from 15 to 25 Torr and at a

EXAMPLE 2

300 g of 4-hydroxy benzoic acid i-octyl ester are added to 545 g of sulphochlorination product containing 6.5% of hydrolysable chlorine, produced from an n-paraffin mixture with a chain length of 10 to 18 carbon atoms under the same conditions as in Example 1, followed by esterification with 240 g of 20% sodium hydroxide and working up in the same way as in Example 1. The yield of ester amounts to 401 g.

| Properties of the ester | | |
|---|---|---|
| Density at 20° C. | (g/cm³) | 1.038 |
| Viscosity at 20° C. | (mPa.s) | 623 |
| crit. dissolution temperature | (°C.) | 145 |
| Cold setting point | (°C.) | −35 |
| Volatility at 90° C. | | |
| 0–72 h | (%) | −0.3 |
| 48–72 h | (%) | ±0 |

| Mechanical properties of the PVC-plasticiser mixtures (65:35) | | |
| --- | --- | --- |
| Shore-hardness | (A/D) | 90/36 |
| Cold fracture temperature | (°C.) | −17 |
| Elongation at break | (%) | 358 |
| Tear propagation resistance | (KN/m) | 76.2 |
| Volatility from the film at 90° C., 72 h | (%) | −0.2 |

| Plasticiser migration in % by weight in rigid PVC and polystyrene films (PS) | | | |
| --- | --- | --- | --- |
| | | after 1 day | after 9 days |
| Plasticiser-absorbing film | PVC | +0.2 | +0.5 |
| | PS | ±0 | +0.1 |
| Plasticiser-releasing film | PVC | −0.2 | −0.6 |
| | PS | −0.1 | −0.2 |

EXAMPLE 3

266 g of 4-hydroxy benzoic acid hexyl ester were added to 885 g of sulphochlorination product containing 4% of hydrolysable chlorine, produced from the same n-paraffin mixture and under the same conditions as in Example 1, followed by esterification with 210 g of 20% sodium hydroxide and working up in the same way as in Example 1. The yield of ester comprise 330 g.

| Properties of the ester | | |
| --- | --- | --- |
| Density at 20° C. | (g/cm$^3$) | 1.035 |
| Viscosity at 20° C. | (mPa.s) | 428 |
| Crit. dissolution temperature | (°C.) | 135 |
| Cold setting point | (°C.) | −26 |
| Volatility at 90° C. | | |
| 0–72 h | (%) | −0.3 |
| 48–72 h | (%) | −0.1 |

| Mechanical properties of the PVC-plasticiser mixtures (65:35) | | |
| --- | --- | --- |
| Shore hardness | (A/D) | 85/32 |
| Cold fracture temperature | (°C.) | −18 |
| Elongation at break | (%) | 352 |
| Tear propagation resistance | (KN/m) | 68.7 |
| Volatility from the film at 90° C., 72 h | (%) | −0.3 |

| Plasticiser migration in % by weight in rigid PVC and polystyrene films (PS) | | | |
| --- | --- | --- | --- |
| Plasticiser-absorbing film | PVC | +0.2 | +1.1 |
| | PS | ±0 | +0.3 |
| Plasticiser-releasing film | PVC | −0.3 | −1.3 |
| | PS | −0.1 | −0.5 |

EXAMPLE 4

115 g of 4-hydroxy benzoic acid-n-butyl ester were added to 445 g of sulphochlorination product containing 4% of hydrolysable chlorine, produced from the same n-paraffin mixture and under the same reaction conditions as described in Example 1, followed by esterification with 110 g of 20% sodium hydroxide solution and working up in the same way as described in Example 1. The yield of ester comprised 180 g.

| Properties of the ester | | |
| --- | --- | --- |
| Density at 20° C. | (g/cm$^3$) | 1.054 |
| Viscosity at 20° C. | (mPa.s) | 250 |
| Crit. dissolution temperature | (°C.) | 127 |
| Cold setting point | (°C.) | −40 |
| Volatility at 90° C. | | |
| 0–72 h | (%) | −0.4 |
| 48–$\eta$h | (%) | −0.2 |

| Mechanical properties of the PVC-plasticiser mixtures (65:35) | | |
| --- | --- | --- |
| Shore-hardness | (A/D) | 83/28 |
| Cold fracture temperature | (°C.) | −30 |
| Elongation at break | (%) | 418 |
| Tear propagation resistance | (KN/m) | 58.9 |
| Volatility from the film at 90° C., 72 h | (%) | −0.8 |

| Plasticiser migration in % by weight in rigid PVC and polystyrene films (PS) | | | |
| --- | --- | --- | --- |
| Plasticiser-absorbing film | PVC | +0.5 | +1.5 |
| | PS | +0.4 | +1.6 |
| Plasticiser-releasing film | PVC | −0.4 | −1.6 |
| | PS | −0.4 | −1.7 |

EXAMPLE 5

233 g of 4-hydroxy benzoic acid-i-butyl ester were added to 530 g of sulphochlorination product containing 6.7% of hydrolysable chlorine, produced from the same n-paraffin mixture and under the same reaction conditions as described in Example 1, followed by esterification with 210 g of 20% sodium hydroxide solution and working up in the same way, as described in Example 1. The yield of ester amounted to 287 g.

| Properties of the ester | | |
| --- | --- | --- |
| Density at 20° C. | (g/cm$^3$) | 1.071 |
| Viscosity at 20° C. | (mPa.s) | 767 |
| Crit. dissolution temperature | (°C.) | 129 |
| Cold setting point | (°C.) | −32 |
| Volatility at 90° C. | | |
| 0–72 h | (%) | −0.3 |
| 48–72 h | (%) | −0.1 |

| Mechanical properties of the PVC-plasticiser mixture (65:35) | | |
| --- | --- | --- |
| Shore-hardness | (A/D) | 85/34 |
| Cold fracture temperature | (°C.) | −10 |
| Elongation at break | (%) | 332 |
| Tear propagation resistance | (KN/m) | 72.9 |
| Volatility from the film at 90° C., 72 h | (%) | −0.2 |

| Plasticiser migration in % by weight in rigid PVC and polystyrene films (PS) | | | |
| --- | --- | --- | --- |
| | | after 1 day | after 9 days |
| Plasticiser-absorbing film | PVC | +0.2 | +1.1 |
| | PS | ±0 | +0.1 |

| -continued | | | |
|---|---|---|---|
| Plasticiser migration in % by weight in rigid PVC and polystyrene films (PS) | | | |
| | | after 1 day | after 9 days |
| Plasticiser-releasing film | PVC | −0.3 | −1.4 |
| | PS | −0.1 | −0.3 |

EXAMPLE 6

323 g of sulphochlorination product containing 11% of hydrolysable chlorine, produced from the same n-paraffin mixture and under the same reaction conditions as described in Example 1, were mixed with 233 g of 4-hydroxy benzoic acid-i-butyl ester, followed by esterification with 210 g of 20% sodium hydroxide solution and further working up in the same way as described in Example 1. The yield of ester amounted to 309 g.

| Properties of the ester | | |
|---|---|---|
| Density at 20° C. | (g/cm$^3$) | 1.092 |
| Viscosity at 20° C. | (mPa.s) | 2170 |
| Crit. dissolution temperature | (°C.) | 130 |
| Cold setting point | (°C.) | −25 |
| Volatility at 90° C. | | |
| 0–72 h | (%) | −0.2 |
| 48–72 h | (%) | ±0 |

| Mechanical properties of the PVC-plasticiser mixture (65:35) | | |
|---|---|---|
| Shore-hardness | (A/D) | 85/35 |
| Cold fracture temperature | (°C.) | −9 |
| Elongation at break | (%) | 338 |
| Tear propagation resistance | (KN/m) | 72.0 |
| Volatility from the film at 90° C., 72 h | (%) | −0.3 |

| Plasticiser migration in % by weight in rigid PVC and polystyrene films (PS) | | | |
|---|---|---|---|
| | | after 1 day | after 9 days |
| Plasticiser-absorbing film | PVC | +0.3 | +0.6 |
| | PS | ±0 | ±0 |
| Plasticiser-releasing film | PVC | −0.3 | −0.8 |
| | PS | −0.1 | −0.1 |

EXAMPLE 7

115 g of 4-hydroxy benzoic acid-n-butyl ester were added to 445 g of sulphochlorination product containing 4% of hydrolysable chlorine, produced from the same n-paraffin mixture and under the same reaction conditions as described in Example 1, and ammonia (4 l/h) introduced onto the surface with stirring for 4 hours at 25° to 30° C. The reaction mixture was then stirred until no more hydrolysable chlorine could be detected. It was then washed at 60° C. with 100 ml of water, twice with 190 ml of 4% sodium hydroxide and then once again with 100 ml of water. Crude ester was obtained in a quantity of 470 g, being worked up in the same way as described in Example 1. The yield of ester amounted to 160 g.

The product and service properties corresponded to those of the ester described in Example 4.

EXAMPLE 8

117 g of 3-hydroxy benzoic acid-i-butyl ester were added to 445 g of sulphochlorination product containing 4% of hydrolysable chlorine, produced from the same n-paraffin mixture and under the same reaction conditions as described in Example 1, followed by esterification with 110 g of 20% sodium hydroxide solution and working up in the same way as described in Example 1. The yield of ester amounted to 150 g.

| Properties of the ester | | |
|---|---|---|
| Density at 20° C. | (g/cm$^3$) | 1.069 |
| Viscosity at 20° C. | (mPa.s) | 773 |
| Crit. dissolution temperature | (°C.) | 126 |
| Cold setting point | (°C.) | −34 |
| Volatility at 90° C. | | |
| 0–72 h | (%) | −0.2 |
| 48–72 h | (%) | −0.2 |

| Mechanical properties of the Pvc-plasticiser mixture (65:35) | | |
|---|---|---|
| Shore-hardness | (A/D) | 85/35 |
| Cold fracture temperature | (°C.) | −16 |
| Elongation at break | (%) | 350 |
| Tear propagation resistance | (KN/m) | 62.0 |
| Volatility from the film at 90° C., 72 h | (%) | −0.4 |

| Plasticiser migration in % by weight in rigid PVC and polystyrene films (PS) | | | |
|---|---|---|---|
| | | after 1 day | after 9 days |
| Plasticiser-absorbing film | PVC | +0.6 | +1.3 |
| | PS | +0.5 | +1.0 |
| Plasticiser-releasing film | PVC | −0.5 | −1.4 |
| | PS | −0.4 | −1.1 |

Example 9

117 g of a 1:1 mixture of 4- and 3-hydroxy benzoic acid-i-butyl ester were added to 445 g of sulphochlorination product containing 4% of hydrolysable chlorine, produced from the same n-paraffin mixture and under the same reaction conditions as described in Example 1, followed by esterification with 110 g of 20% sodium hydroxide solution and working up in the same way as described in Example 1. The yield of ester amounted to 156 g.

| Properties of the ester | | |
|---|---|---|
| Density at 20° C. | (g/cm$^3$) | 1.069 |
| Viscosity at 20° C. | (mPa.s) | 770 |
| Crit. dissolution temperature | (°C.) | 127 |
| Cold setting point | (°C.) | −38 |
| Volatility at 90° C. | | |
| 0–72 h | (%) | −0.3 |
| 48–72 h | (%) | −0.2 |

| Mechanical properties of the PVC-plasticiser mixture (65:35) | | |
|---|---|---|
| Shore-hardness | (A/D) | 82/28 |
| Cold fracture temperature | (°C.) | −18 |
| Elongation at break | (%) | 370 |
| Tear propagation resistance | (KN/m) | 60.2 |

| Mechanical properties of the PVC-plasticiser mixture (65:35) | | |
|---|---|---|
| -continued | | |
| Volatility from the film at 90° C., 72 h | (%) | −0.3 |

| Plasticiser migration in % by weight in rigid PVC and polystyrene film (PS) | | after 1 day | after 9 days |
|---|---|---|---|
| Plasticiser-absorbing film | PVC | +0.5 | +1.4 |
| | PS | +0.4 | +1.2 |
| Plasticiser-releasing film | PVC | −0.4 | −1.5 |
| | PS | −0.3 | −1.3 |

EXAMPLE 10

420 g of sulphochlorination product containing 8.4% of hydrolysable chlorine, produced from an n-paraffin mixture with a chain length of 10 to 13 carbon atoms under the same sulphochlorination conditions as described in Example 1, were mixed with 233 g of 4-hydroxy benzoic acid-i-butyl ester, followed by esterification with 210 g of 20% sodium hydroxide and working up in the same way as described in Example 1. The yield of ester amounted to 338 g.

| Properties of the ester | | |
|---|---|---|
| Density at 20° C. | (g/cm³) | 1.094 |
| Viscosity at 20° C. | (mPa.s) | 2155 |
| Crit. dissolution temperature | (°C.) | −8 |
| Cold setting point | (°C.) | 131 |
| Volatility at 90° C. | | |
| 0–72 h | (%) | −0.3 |
| 48–72 h | (%) | −0.1 |

| Mechanical properties of the PVC-plasticiser mixture (65:35) | | |
|---|---|---|
| Shore-hardness | (A/D) | 89/40 |
| Cold fracture temperature | (°C.) | ±0 |
| Elongation at break | (%) | 330 |
| Tear propagation resistance | (KN/m) | 87.7 |
| Volatility from the film at 90° C., 72 h | (%) | −0.2 |

| Plasticiser migration in % by weight in rigid PVC and polystyrene films (PS) | | after 1 day | after 9 days |
|---|---|---|---|
| Plasticiser-absorbing film | PVC | +0.7 | +1.5 |
| | PS | +0.1 | +0.2 |
| Plasticiser-releasing film | PVC | −0.7 | −1.6 |
| | PS | −0.1 | −0.3 |

EXAMPLE 11

445 g of sulphochlorination product containing 4% of hydrolysable chlorine, produced from the same n-paraffin mixture and under the same reaction conditions as described in Example 1, were mixed with 99 g of 4-hydroxy benzoic acid ethyl ester, followed by esterification with 110 g of 20% sodium hydroxide and working up in the same way as described in Example 1. The yield of ester amounted to 172 g.

| Properties of the ester | | |
|---|---|---|
| Density at 20° C. | (g/cm³) | 1.067 |
| Viscosity at 20° C. | (mPa.s) | 276 |
| Crit. dissolution temperature | (°C.) | 125 |
| Cold setting point | (°C.) | −41 |
| Volatility at 90° C. | | |
| 0–72 h | (%) | ±0 |
| 48–72 h | (%) | ±0 |

| Mechanical properties of the PVC-plasticiser mixture (65:35) | | |
|---|---|---|
| Shore-hardness | (A/D) | 81/27 |
| Cold fracture temperature | (°C.) | −17 |
| Elongation at break | (%) | 322 |
| Tear propagation resistance | (KN/m) | 68.3 |
| Volatility from the film at 90° C., 72 h | (%) | −0.2 |

| Plasticiser migration in % by weight in rigid PVC and polystyrene films (PS) | | after 1 day | after 9 days |
|---|---|---|---|
| Plasticiser-absorbing film | PVC | +0.6 | −0.7 |
| | PS | +0.2 | −0.3 |
| Plasticiser-absorbing film | PVC | +2.1 | −2.2 |
| | PS | +1.1 | −1.2 |

I claim:

1. A compound of the formula

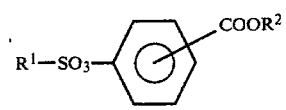

wherein $R^1$ is alkyl having 10 to 18 carbon atoms and $R^2$ is alkyl having 1 to 12 carbon atoms.

2. A compound of claim 1 wherein $R^1$ is alkyl having 10 to 13 carbon atoms.

3. A compound of claim 1 wherein $R^2$ is alkyl having 2 to 8 carbon atoms.

4. A composition comprising a polymer plasticized with a compound of claim 1 said polymer being selected from the group consisting of polyvinyl chloride, natural rubber, synthetic rubber and a copolymer of vinyl chloride with a member selected from the group consisting of a vinyl ester, an olefin, α,β-unsaturated monocarboxylic acid ester and α,β-unsaturated dicarboxylic acid ester.

5. A method of plasticizing a polymer which comprises incorporating in said polymer a plasticizing amount of a compound of claim 1, said polymer being selected from the group consisting of polyvinyl chloride, natural rubber, synthetic rubber and a copolymer of vinyl chloride with a member selected from the group consisting of a vinyl ester, olefin, α,β-unsaturated monocarboxylic acid ester and α,β-unsaturated dicarboxylic acid ester.

6. The composition of matter of claim 4 wherein said plasticizer is present in an amount of from 1 to 70 parts by weight per 100 parts by weight of polymer.